United States Patent
Han et al.

(10) Patent No.: US 8,873,131 B2
(45) Date of Patent: Oct. 28, 2014

(54) ACOUSTO-OPTIC DEVICE HAVING MULTI-LAYER NANOSTRUCTURE, OPTICAL SCANNER, OPTICAL MODULATOR, AND DISPLAY APPARATUS USING THE ACOUSTO-OPTIC DEVICE

(75) Inventors: Seung-hoon Han, Seoul (KR); Wan-joo Maeng, Seoul (KR); Sang-yoon Lee, Seoul (KR); Hong-seok Lee, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 172 days.

(21) Appl. No.: 13/533,353

(22) Filed: Jun. 26, 2012

(65) Prior Publication Data

US 2013/0003066 A1  Jan. 3, 2013

(30) Foreign Application Priority Data

Jun. 28, 2011 (KR) .................. 10-2011-0063045

(51) Int. Cl.
*G02F 1/33* (2006.01)
*G02F 1/00* (2006.01)

(52) U.S. Cl.
CPC .............. *G02F 1/33* (2013.01); *G02F 2202/32* (2013.01); *G02F 2203/10* (2013.01); *G02F 1/0072* (2013.01)
USPC ....................................................... 359/305

(58) Field of Classification Search
CPC ....................................................... G02F 1/33
USPC ......................................... 359/305; 356/342
See application file for complete search history.

(56) References Cited

U.S. PATENT DOCUMENTS

| 5,130,843 | A * | 7/1992 | He et al. ................. 359/285 |
| 5,657,152 | A | 8/1997 | Kadota |
| 5,900,966 | A | 5/1999 | Kim et al. |
| 6,853,474 | B2 | 2/2005 | Yu et al. |
| 2001/0026659 | A1 | 10/2001 | Sekine et al. |
| 2012/0194885 | A1* | 8/2012 | Han et al. ................. 359/10 |

FOREIGN PATENT DOCUMENTS

| EP | 2-482-121 | A1 | 1/2012 |
| KR | 1998-029976 | A | 7/1998 |
| KR | 10-0425682 | B1 | 4/2004 |
| KR | 10-2012-0087631 | A | 8/2012 |

OTHER PUBLICATIONS

European Search Report issued Nov. 21, 2012 in counterpart European Patent Application No. 12172114.6-1228 (7 pages, in English).
Thompson, Cameron et al. "Acoustooptic Interactions in AlGaAs—GaAs Planar Multilayer Waveguide Structures," IEEE Journal of Quantum Electronics, vol. 33, No. 9, Sep. 1997, pp. 1601-1607 (7 pages, in English).

* cited by examiner

*Primary Examiner* — James Jones
(74) *Attorney, Agent, or Firm* — NSIP Law (57) ABSTRACT

An acousto-optic device includes an acousto-optic medium having a multi-layer nanostructure; and a sonic wave generator configured to apply sonic waves to the acousto-optic medium having the multi-layer nanostructure. The acousto-optic medium having the multi-layer nanostructure includes a second layer formed of at least two materials that have different dielectric constants and alternate with each other; and a first layer disposed on a first surface of the second layer and formed of a first material, and/or a third layer disposed on a second surface of the second layer and formed of a fourth material.

35 Claims, 6 Drawing Sheets

FIG. 10B

ACOUSTO-OPTIC DEVICE HAVING MULTI-LAYER NANOSTRUCTURE, OPTICAL SCANNER, OPTICAL MODULATOR, AND DISPLAY APPARATUS USING THE ACOUSTO-OPTIC DEVICE

CROSS-REFERENCE TO RELATED APPLICATIONS

This application claims the benefit of Korean Patent Application No. 10-2011-0063045 filed on Jun. 28, 2011, in the Korean Intellectual Property Office, the disclosure of which is incorporated herein by reference in its entirety.

BACKGROUND

1. Field

This disclosure relates to acousto-optic devices having multi-layer nanostructures, and to optical scanners, optical modulators, and display apparatuses using the acousto-optic devices, and more particularly, to an acousto-optic device capable of increasing a range of a diffraction angle of output light or adjusting a diffraction angle characteristic of the output light by using an acousto-optic medium having a multi-layer nanostructure formed of metal and dielectric materials, and to an optical scanner, an optical modulator, and a display apparatus using the acousto-optic device.

2. Description of the Related Art

The acousto-optic effect is an effect in which a refractive index of light is periodically varied in a medium by a series of compressions and rarefactions in the medium produced by sonic waves such as ultrasonic waves propagating in the medium. The series of compressions and rarefactions produces a phase grating in the medium, which diffracts light incident on the medium. In general, a medium exhibiting the acousto-optic effect is called an acousto-optic medium. An intensity and a diffraction angle of diffracted light produced by the phase grating in the medium depend on an intensity of the sonic waves and a frequency of the sonic waves, respectively. Thus, an acousto-optic device having a sonic wave generator such as an ultrasonic wave generator on a surface of the medium having the aforementioned characteristic may be used in an optical modulator for modulating the amplitude of incident light, or in an optical scanner for deflecting incident light.

However, acousto-optic devices that use raw mediums existing in the natural world have a limited range of a diffraction angle of output light due to a limited optical anisotropy and a limited acousto-optic coefficient of the mediums. That is, in an acousto-optic according to the related art, a range of a diffraction angle of output light is too narrow. Thus, when an acousto-optic device according to the related art is used in various optical application fields, including an optical scanner, an optical modulator, a display or the like, a separate optical system is required to compensate for the narrow range of the diffraction angle. This separate optical system increases a size of the system and/or may reduce a resolution of the system. Accordingly, research into various structures of the acousto-optic medium and an increase in a range of a diffraction angle of the acousto-optic device have been conducted.

SUMMARY

According to an aspect, an acousto-optic device including an acousto-optic medium having a multi-layer nanostructure; and a sonic wave generator configured to apply sonic waves to the acousto-optic medium having the multi-layer nanostructure; wherein the acousto-optic medium having the multi-layer nanostructure includes a second layer formed of at least two materials that have different dielectric constants and alternate with each other; and a first layer disposed on a first surface of the second layer and formed of a first material, and/or a third layer disposed on a second surface of the second layer and formed of a fourth material.

The second layer may include a second material and a third material that repeatedly alternate with each other; and the first material, the second material, the third material, and the fourth materials may include a combination of at least two materials selected from the group consisting of a gain material having a gain characteristic enabling optical amplification of light; an acousto-optic material exhibiting an acousto-optic effect; a dielectric that is not a gain material and is not an acousto-optic material; and a material having a dielectric constant with a real part having a negative value.

The gain material having a gain characteristic enabling the optical amplification of light may include at least one material selected from the group consisting of a group III-V semiconductor selected from the group consisting of GaN, $Al_{1-x}Ga_xN$, and $In_{1-x}Ga_xN$ ($0<x<1$), a quantum well structure or a quantum dot structure including the group III-V semiconductor, zinc oxide, CdS, an organic crystal, and a gain dye.

The dielectric that is not a gain material and is not an acousto-optic material may include at least one material selected from the group consisting of $SiO_2$ and air.

The material having a dielectric constant with a real part having a negative value may include one material selected from the group consisting of a metal selected from the group consisting of Al, Ag, Au, Cu, Na, Ka, and an alloy of any one or more of Al, Ag, Au, Cu, Na, and Ka, an oxide selected from the group consisting of indium tin oxide (ITO), aluminum-doped zinc oxide (AZO), gallium zinc oxide (GZO), and indium zinc oxide (IZO), a nitride selected from the group consisting of titanium nitride (TiN), zirconium nitride (ZrN), tantalum nitride (TaN), and hafnium nitride (HfN), and graphene.

The second material and the third material may have different dielectric constants; and at least one of the first material, the second material, the third material, and the fourth material may have a dielectric constant with a real part having a negative value.

The second layer may include a plurality of pieces of the second material and a plurality of pieces of the third material that repeatedly alternate with each other in a direction parallel to the first surface of the second layer and the second surface of the second layer.

A period at which the plurality of pieces of the second material and the plurality of pieces of the third material repeatedly alternate with each other may be smaller than a wavelength of visible light in air.

An aspect ratio of each piece of the second material and an aspect ratio of each piece of the third material may be not greater than 4.

Each piece of the second material and each piece of the third material may have a bar shape.

The sonic wave generator may be disposed on a side surface of the acousto-optic medium having the multi-layer nanostructure that is perpendicular to the first surface of the second layer and the second surface of the second layer.

The acousto-optic device of claim 1 may further include a substrate contacting at least a side surface of the acousto-optic medium having the multi-layer nanostructure that is perpendicular to the first surface of the second layer and the second surface of the second layer; and the sonic wave generator may be disposed on a surface of the substrate that is parallel to the first surface of the second layer and the second surface of the second layer adjacent to the side surface of the acousto-optic medium having the multi-layer nanostructure.

The second layer may include a plurality of pieces of the second material and a plurality of pieces of the third material that repeatedly alternate with each other in a direction perpendicular to the first surface of the second layer and the second surface of the second layer.

Each of the first material, the second material, the third material, and the fourth material may include a material selected from the group consisting of a gain material having a gain characteristic enabling optical amplification of light, an acousto-optic material exhibiting an acousto-optic effect, a dielectric that is not a gain material and is not an acousto-optic material, and a material having a dielectric constant with a real part having a negative value; the second material and the third material may have different dielectric constants; and the second material or the third material may have a dielectric constant with a real part having a negative value.

The second layer may include a second material, and a third material having a different dielectric constant than the second material and regularly arranged in the second material.

The acousto-optic device may further include an optical coupling device configured to guide light incident onto the acousto-optic medium having the multi-layer nanostructure to enable the light to propagate in the second layer.

The optical coupling device may include a prism or a diffraction grating layer disposed on a surface of the acousto-optic medium having the multi-layer nanostructure.

According to an aspect, a two-dimensional/three-dimensional (2D/3D) conversion stereoscopic image display apparatus includes a display panel; and an acousto-optic device array disposed on a surface of the display panel to deflect an image to be displayed on the display panel; wherein the acousto-optic device array includes a plurality of the acousto-optic device described above.

Each of the plurality of acousto-optic devices of the acousto-optic device array may extend in a horizontal direction; and the plurality of acousto-optic devices may be arrayed in a vertical direction.

Each of the plurality of acousto-optic devices of the acousto-optic device array may correspond to one pixel row of the display panel.

According to an aspect, a holographic display apparatus includes a light source configured to emit light; an acousto-optic device array configured to deflect the light emitted from the light source, and including a plurality of the acousto-optic device described above; and a projection optical system configured to project the light deflected by the acousto-optic device array.

Each of the plurality of acousto-optic devices of the acousto-optic device array may extend in a horizontal direction; and the plurality of acousto-optic devices may be arrayed in a vertical direction.

The plurality of acousto-optic devices may generate hologram rows in a horizontal direction of a hologram image displayed by the holographic display apparatus; and each of the plurality of acousto-optic devices may correspond to one of the hologram rows.

According to an aspect, a sensor includes the acousto-optic device described above; a container disposed on a surface of the acousto-optic medium having the multi-layer nanostructure and configured to contain a sample; and an optical detector configured to detect light diffracted in a combination of the acousto-optic medium having the multi-layer nanostructure and the sample in the container.

According to an aspect, an optical scanner includes a substrate; a first acousto-optic device; a second acousto-optic device; and an optical coupling device configured to make light incident on the first acousto-optic device; wherein the first acousto-optic device includes a first acousto-optic medium disposed in the substrate; and a first sonic wave generator disposed on a surface of the substrate adjacent to a side surface of the first acousto-optic medium that is perpendicular to the surface of the substrate; the second acousto-optic device includes a second acousto-optic medium disposed in the substrate and adjacent to the first acousto-optic medium; and a second sonic wave generator disposed on the surface of the substrate adjacent to a side surface of the second acousto-optic that is perpendicular to the surface of the substrate; each of the first acousto-optic medium and the second acousto-optic medium includes a second layer formed of at least two materials that have different dielectric constants and alternate with each other; and a first layer disposed on a first surface of the second layer and formed of a first material, and/or a third layer disposed on a second surface of the second layer and formed of a fourth material; and the first surface of the second layer and the second surface of the second layer are parallel to the surface of the substrate.

The second layer may include a plurality of pieces of the second material and a plurality of pieces of the third material that repeatedly alternate with each other; and the first material, the second material, the third material, and the fourth material may include a combination of at least two materials selected from the group consisting of a gain material having a gain characteristic enabling optical amplification of light; an acousto-optic material exhibiting an acousto-optic effect; a dielectric material that is not a gain material and is not an acousto-optic material; and a material having a dielectric constant with a real part having a negative value.

The plurality of pieces of the second material and the plurality of pieces of the third material may repeatedly alternate with each other in a direction parallel to the first surface of the second layer and the second surface of the second layer; the second material and the third may have different dielectric constants; and at least one of the first material, the second material, the third material, and the fourth material may have a dielectric constant with a real part having a negative value.

The plurality of pieces of the second material and the plurality of pieces of the third material may repeatedly alternate with each other in a direction perpendicular to the first surface of the second layer and the second surface of the second layer; the second material and the third material may have different dielectric constants; and at least one of the first material, the second material, the third material, and the fourth material may have a dielectric constant with a real part having a negative value.

The first acousto-optic device may be configured to deflect incident light in a first direction; and the second acousto-optic device may be configured to deflect the incident light deflected by the first acousto-optic device in a second direction perpendicular to the first direction.

According to an aspect, a acousto-optic device includes an acousto-optic medium; and a sonic wave generator configured to apply sonic waves to the acousto-optic medium; wherein the acousto-optic medium includes a first layer including a first material and a second material that have different dielectric constants and alternate with each other to form a nanostructure in the first layer; and a second layer contacting a surface of the first layer and including a third material.

The first material and the second material may alternate with each other at a period that is smaller than a wavelength of light to be controlled by the acousto-optic device.

At least one of the first material, the second material, and the third material may include a metal; and at least one of the first material, the second material, and the third material may not include a metal.

The metal may be selected from the group consisting of Al, Ag, Au, Cu, Na, Ka, and an alloy of any one or more of Al, Ag, Au, Cu, Na, and Ka.

The acousto-optic medium may generate surface plasmons in an interface between the first layer and the second layer from light that is incident on the acousto-optic medium.

The first material, the second material, and the third material may include a combination of at least two materials selected from the group consisting of a gain material having a gain characteristic enabling optical amplification of light; an acousto-optic material exhibiting an acousto-optic effect; a dielectric that is not a gain material and is not an acousto-optic material; and a material having a dielectric constant with a real part having a negative value.

Additional aspects will be set forth in part in the description that follows and, in part, will be apparent from the description, or may be learned by practice of the described examples.

BRIEF DESCRIPTION OF THE DRAWINGS

The above and other aspects will become apparent and more readily appreciated from the following description of examples, taken in conjunction with the accompanying drawings of which.

DETAILED DESCRIPTION

Reference will now be made in detail to examples of an acousto-optic device having a multi-layer nanostructure, and an optical scanner, an optical modulator, and a display apparatus using the acousto-optic device, examples of which are illustrated in the accompanying drawings. In the drawings, like reference numerals denote like elements, and the size of each element may be exaggerated for clarity.

Figure 1:
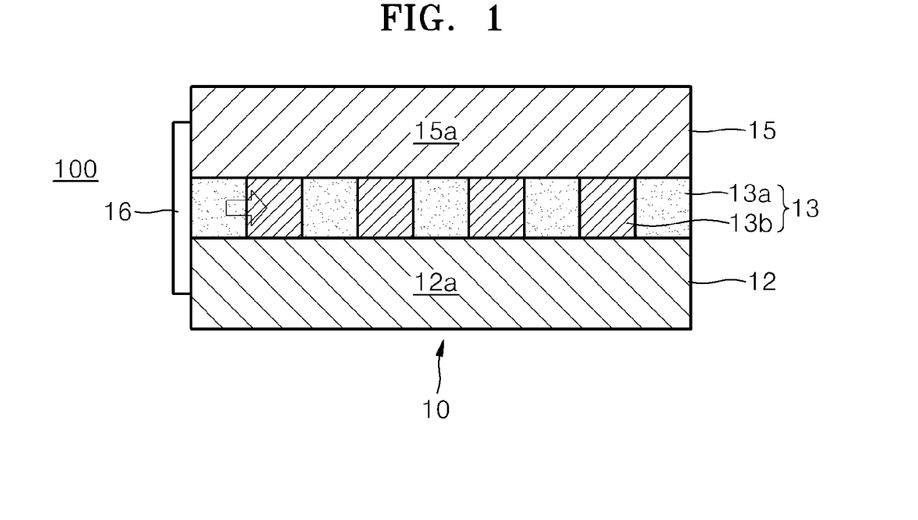
FIG. 1 is a cross-sectional view of a schematic structure of an acousto-optic device according to an example of the invention.

FIG. 1 is a cross-sectional view of a schematic structure of an acousto-optic device 100 according to an example of the invention. Referring to FIG. 1, the acousto-optic device 100 includes an acousto-optic medium 10 having a multi-layer nanostructure and a sonic wave generator 16 for applying sonic waves to the acousto-optic medium 10. As used herein, the term "nanostructure" denotes a structure having elements having a dimension generally on the order of 5 nm to 500 nm, but is not limited to this exact range.

The acousto-optic medium 10 having the multi-layer nanostructure includes a first layer 12 formed of a first material 12a, a second layer 13 formed of a second material 13a and a third material 13b that have different dielectric constants and are alternately disposed, and a third layer 15 formed of a fourth material 15a. The first layer 12 and the third layer 15 are disposed facing each other. The second layer 13 is interposed between the first layer 12 and the third layer 15. The second material 13a and the third material 13b of the second layer 13 alternate with each other between the first layer 12 and the third layer 15 in a horizontal direction (i.e., a direction parallel to surfaces of the first layer 12 and the third layer 15) to form a nanostructure in the second layer 13. A period at which the second material 13a and the third material 13b alternate with each other may be smaller than a wavelength (e.g., a wavelength in air) of light (e.g., visible light) to be controlled by the acousto-optic device 100. For example, the period may be smaller than the wavelength of the light to be controlled by the acousto-optic device 100.

Although FIG. 1 shows both the first layer 12 and the third layer 15, only one of the first layer 12 and the third layer 15 may be disposed according to another example. For example, the acousto-optic medium 10 may include the first layer 12 and the second layer 13, or may include the second layer 13 and the third layer 15. Although two materials (the first material 13a and the second material 13b) alternate with each other in FIG. 1, three or more mediums (for example, three mediums) having different dielectric constants may alternate with each other.

The first through fourth materials 12a, 13a, 13b, and 15a may have, for example, at least one of a gain characteristic enabling optical amplification of light, an acousto-optic characteristic exhibiting an acousto-optic effect, and a characteristic in which a real part of a dielectric constant has a negative value.

Materials having the characteristic in which a real part of a dielectric constant has a negative value include, for example, a metal such as Al, Ag, Au, Cu, Na, Ka, or an alloy of any one or more of Al, Ag, Au, Cu, Na, and Ka. Other materials having the characteristic in which a real part of a dielectric constant has a negative value include, for example, an oxide such as indium tin oxide (ITO), aluminum-doped zinc oxide (AZO), gallium zinc oxide (GZO), indium zinc oxide (IZO), or the like, a nitride such as titanium nitride (TiN), zirconium nitride (ZrN), tantalum nitride (TaN), hafnium nitride (HfN), or the like, and graphene, etc. Other materials having the characteristic in which a real part of a dielectric constant has a negative value are regarded as being included in a range of metals hereinafter.

Gain materials having the gain characteristic enabling optical amplification of light include, for example, group III-V semiconductors including GaN, $Al_{1-x}Ga_xN$, and $In_{1-x}Ga_xN$ ($0<x<1$), a quantum well structure or a quantum dot structure including the group III-V semiconductors, zinc oxide (ZnO), CdS, an organic crystal such as an excited-state intramolecular proton-transfer material, a gain dye such as rhodamine B and rhodamine 800 (Rh800), and the like.

Materials having the acousto-optic characteristic exhibiting an acousto-optic effect include, for example, $LiNbO_3$, ZnO, GaN, etc.

A transparent dielectric such as $SiO_2$ which is a general dielectric that does not have a gain characteristic and does not have an acousto-optic characteristic may be used as one or more of the first through fourth materials 12a, 13a, 13b, and 15a. The invention is not limited as to types of dielectric materials. For example, air can be used as a dielectric.

The first through fourth materials 12a, 13a, 13b, and 15a may include any combination of a gain material, an acousto-optic material, a dielectric (hereinafter referred to as a dielectric other than a gain material and an acousto-optic material), and a metal. At least two of the first through fourth materials 12a, 13a, 13b, and 15a may be the same. However, the second material 13a and the third material 13b that alternate with each other have different dielectric constants. For example, the second material 13a and the third material 13b may include dielectrics having different dielectric constants, or the second material 13a may include a metal and the third material 13b may include a dielectric, or the second material 13a may include a gain material and the third material 13b may include a metal. Furthermore, although it is not necessary that the first through fourth materials 12a, 13a, 13b, and 15a include a gain material and an acousto-optic material and a dielectric, at least one of the first through fourth materials 12a, 13a, 13b, and 15a must include a metal in order to generate surface plasmons as will be described below.

As described above, the acousto-optic medium 10 of FIG. 1 may include a combination of various materials that may be selected from a wide variety of materials with a high degree of freedom. Thus, the acousto-optic medium 10 may be designed in various ways according to a characteristic as required. As an example, the first layer 12 of the acousto-optic medium 10 of FIG. 1 may include a gain material, the second material 13a and the third material 13b of the second layer 13 may include a metal and a transparent dielectric, respectively, and the third layer 15 may include air. In this case, a height of the second layer 13 may be, for example, between about 50 nm and about 300 nm, and a period at which the second material 13a and the third material 13b alternate with each other may be, for example, between about 50 nm and about 300 nm. Furthermore, an aspect ratio (i.e., a ratio of a height with respect to a width) of the second material 13a and the third material 13b may be approximately 4 or below. Therefore, the aspect ratio is not greater than 4, and thus the second layer 13 may be relatively easily manufactured.

The sonic wave generator 16 may be disposed on a side surface of the acousto-optic medium 10. For example, as indicated by an arrow in FIG. 1, the sonic wave generator 16 is disposed on a side surface of the acousto-optic medium 10 in such a way that sonic waves are applied in a horizontal direction in which the second material 13a and the third material 13b alternate with each other. However, a location of the sonic wave generator 16 may vary in different examples.

Figure 2:
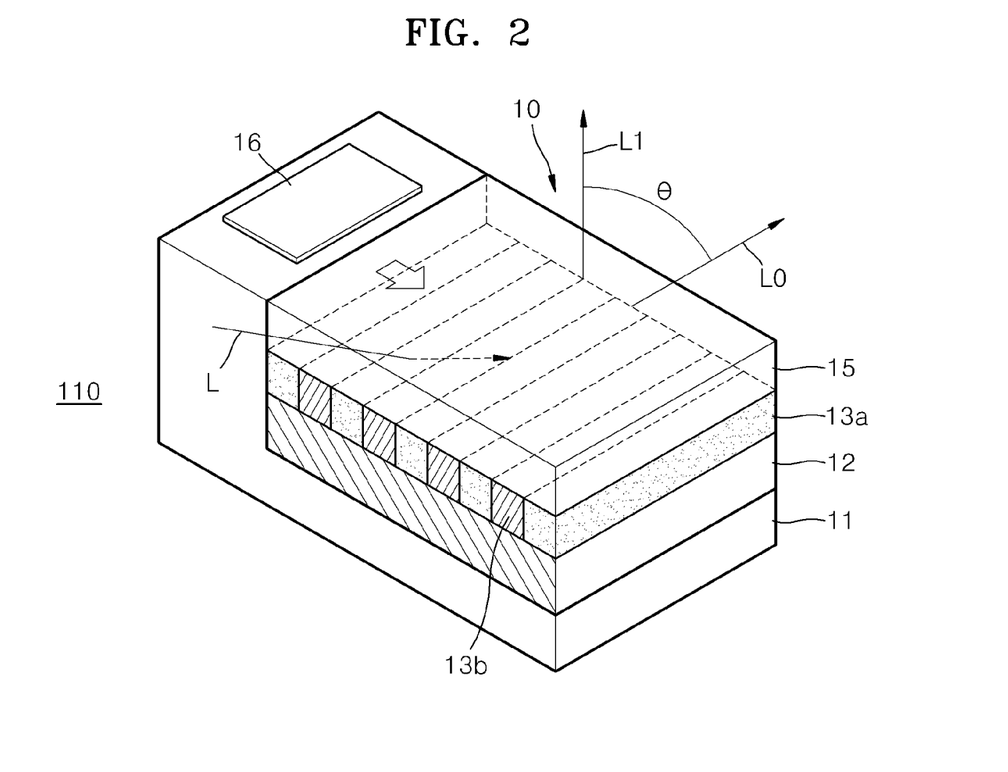
FIG. 2 is a perspective view of a schematic structure of an acousto-optic device according to an example of the invention.

FIG. 2 is a perspective view of a schematic structure of an acousto-optic device 110 according to an example of the invention. Referring to FIG. 2, the acousto-optic device 110 includes the acousto-optic medium 10 having the same structure as shown in FIG. 1, a substrate 11 that contacts at least a bottom portion or one side surface of the acousto-optic medium 10, and the sonic wave generator 16 disposed on a top surface of the substrate 11 adjacent to one side surface of the acousto-optic medium 10. As shown in FIG. 2, the second material 13a and the third material 13b of the second layer 13 have a bar shape to alternate with each other. The sonic wave generator 16 does not necessarily directly contact the surface of the acousto-optic medium 10 as shown in FIG. 1, but may be adjacent to the acousto-optic medium 10 with a medium (the substrate 11 in FIG. 2) for applying sonic waves disposed therebetween.

The operation of the acousto-optic device 110 of FIG. 2 will now be described in detail below. The operation of the acousto-optic device 110 is also applicable to the acousto-optic device 100 of FIG. 1 and acousto-optic devices according to other examples that will be described later. Referring to FIG. 2, when an electrical signal is applied to the sonic wave generator 16 disposed on the top surface substrate 11 adjacent to one side surface of the acousto-optic medium 10, sonic waves such as ultrasonic waves having a predetermined amplitude and frequency are generated in response to the electrical signal. As illustrated in FIG. 2 by an arrow, the sonic waves generated by the sonic wave generator 16 propagate in the acousto-optic medium 10 at a predetermined speed. The sonic waves propagating in the acousto-optic medium 10 produce a series of compressions and rarefactions in the acousto-optic medium 10. The series of periodic compressions and rarefactions cause a local density in the acousto-optic medium 10 vary, which in turn causes a local refractive index of the acousto-optic medium 10 to vary. Accordingly, when the sonic waves propagate in the acousto-optic medium 10, the refractive index of the acousto-optic medium 10 periodically varies in a propagation direction of the sonic waves according to a wavelength of the sonic waves. That is, in response to the periodic series of compressions and rarefactions produced the sonic waves, the refractive index of the acousto-optic medium 10 is periodically increased by the compressions and decreased by the rarefactions. The periodic variation of the refractive index of the acousto-optic medium 10 forms a phase grating having a periodic shape in the acousto-optic medium 10.

The acousto-optic medium 10 having the multi-layer nanostructure including the first through third layers 12, 13, and 15 may serve as a slab waveguide for light or surface plasmons. More specifically, light L incident onto the acousto-optic medium 10 propagates in the second layer 13, or in an interface between the second layer 13 and the first layer 12, or in an interface between the second layer 13 and the third layer 15. The propagating light generates surface plasmons in an interface between a metal and a dielectric included in the acousto-optic medium 10. The surface plasmons are electromagnetic waves that are generated in the interface between the metal and the dielectric. When light is incident onto the interface between the metal and dielectric, the surface plasmons are generated by a charge density oscillation of electrons that occur on a surface of the metal. For example, if the first layer 12 includes a gain material, the second material 13a and the third material 13b of the second layer 13 include a metal and a transparent dielectric, respectively, and the third layer 15 includes air, the surface plasmons may be produced in an interface between the second layer 13 and the first layer 12, and an interface between the second layer 13 and the third layer 15.

If the light L is incident onto the acousto-optic medium 10 having a structure that is sufficiently smaller than a wavelength of the light L in a specific direction and propagates in a surface plasmon state, the acousto-optic medium 10, like a birefringent material, has an anisotropy in which a refractive index greatly differs according to a propagation direction of the surface plasmons. If sonic waves propagate into the acousto-optic medium 10 in which the surface plasmons are propagating, the light in the surface plasmon state will be greatly diffracted while propagating in the second layer 13 due to the strong anisotropy of the refractive index. This is because an angle range of a diffracting operation that satisfies constructive interference of diffracted light increases. Therefore, the acousto-optic medium 10 having the multi-layer nanostructure provides an operating range of a diffraction angle that is higher than an acousto-optic medium that does not have the multi-layer nanostructure. In this regard, the diffraction angle may be defined as an angle difference θ between a 0th order diffraction light L0 and a 1st order diffraction light L1 among light diffracted by the acousto-optic medium 10. A diffraction angle and an intensity of diffracted light produced by the acousto-optic medium 10 may be controlled according to a frequency and an intensity of the sonic waves, respectively. Also, the frequency and intensity of the sonic waves may be determined according to an amplitude and a frequency of the electrical signal that is applied to the sonic wave generator 16. Thus, it is possible to control diffraction of light in the acousto-optic medium 10 by appropriately controlling the electrical signal applied to the sonic wave generator 16.

According to this example, one of the first through fourth materials 12a, 13a, 13b, and 15a includes a gain material, thereby compensating for a light loss. For example, if the first layer 12 includes a gain material, a metal waveguide loss of the surface plasmons can be compensated for by injecting energy into the first layer 12 and activating the gain material to perform optical amplification in an optical or electrical way. The optical amplification may be achieved via optical pumping by shining light having a different wavelength than the wavelength of the light being controlled by the acousto-optic device 10 onto the acousto-optic device 10. Alternatively, the optical amplification may be achieved via electrical pumping by applying an electric field to the acousto-optic device 10 via electrodes provided on the acousto-optic device 10. Therefore, a strong anisotropy of the refractive index can be maintained throughout the entire region of the acousto-optic medium 10. Therefore, an intensity of the 0th order diffraction light L0 and an intensity of the 1st order diffraction light L1 can be increased by compensating for a light loss that occurs when the incident light L propagates in the second layer 13.

In the examples of FIGS. 1 and 2, the second material 13a and the third material 13b of the second layer 13 have a bar shape, and are disposed alternately with each other between the first layer 12 and the third layer 15 in the horizontal direction (i.e., the direction parallel to the surfaces of the first layer 12 and the third layer 15). However, the invention is not limited thereto.

Figure 3:
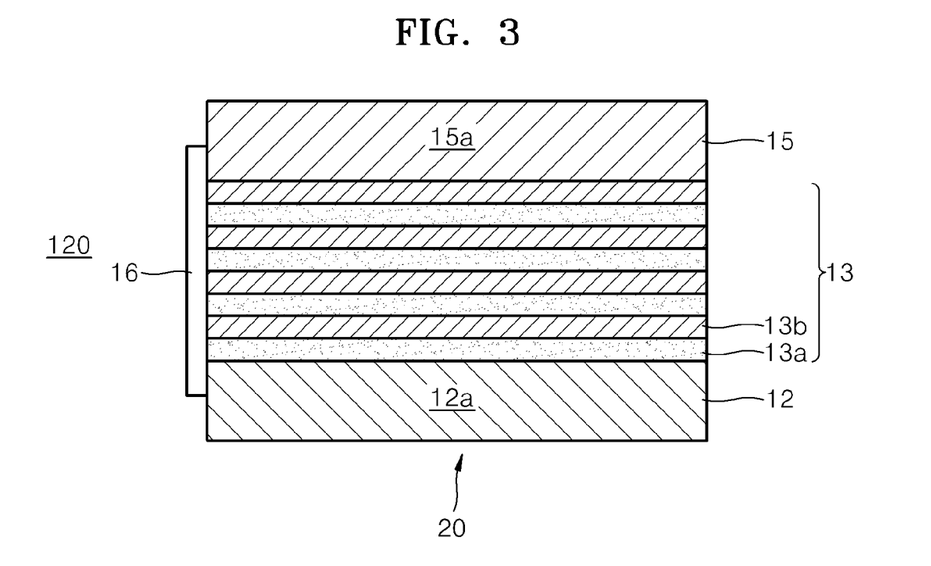
FIG. 3 is a cross-sectional view of a structure of an acousto-optic device according to an example of the invention.
Figure 4:
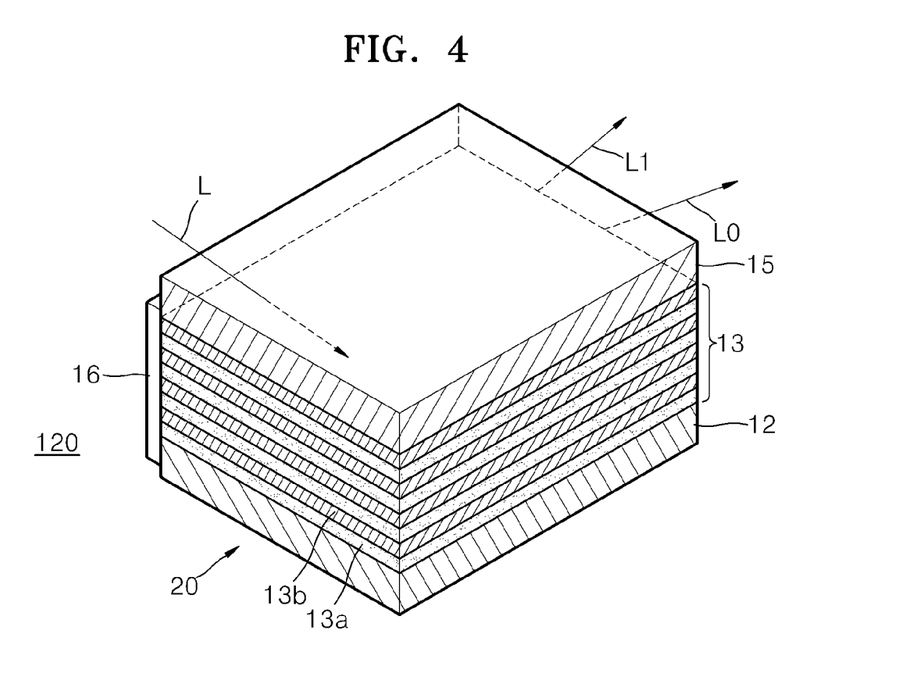
FIG. 4 is a perspective view of a schematic structure of the acousto-optic device of FIG. 3 according to an example of the invention.

FIGS. 3 and 4 are cross-sectional and perspective views, respectively, of a structure of an acousto-optic device 120 according to an example of the invention. Referring to FIGS. 3 and 4, the second material 13a and the third material 13b have thin plate shapes, and are disposed alternately with each other between the first layer 12 and the third layer 15 in a vertical direction (i.e., a direction perpendicular to the surfaces of the first layer 12 and the third layer 15). Thus, an acousto-optic medium 20 of FIGS. 3 and 4 includes the first layer 12 formed of the first material 12a, the second layer 13 that is formed on the first layer 12 and is formed of the second material 13a and the third material 13b that are repeatedly stacked alternately, and the third layer 15 that is formed on the second layer 13 and is formed of the fourth material 15a.

In the acousto-optic device 120, the second material 13a or the third material 13b may include a metal in order to generate surface plasmons in the second layer 13. The remainder of the construction and the operation of the acousto-optic device 120 of FIGS. 3 and 4 may be the same as that of the acousto-optic devices 100 and 110 of FIGS. 1 and 2. Although the sonic wave generator 16 of FIGS. 3 and 4 is disposed directly on one side surface of the acousto-optic medium 20, the sonic wave generator 16 may be disposed on a top surface of a substrate as shown in FIG. 2.

The second layer 13 including the second material 13a and the third material 13b that alternate with each other may be implemented in various ways as described above and below.

Figure 5:
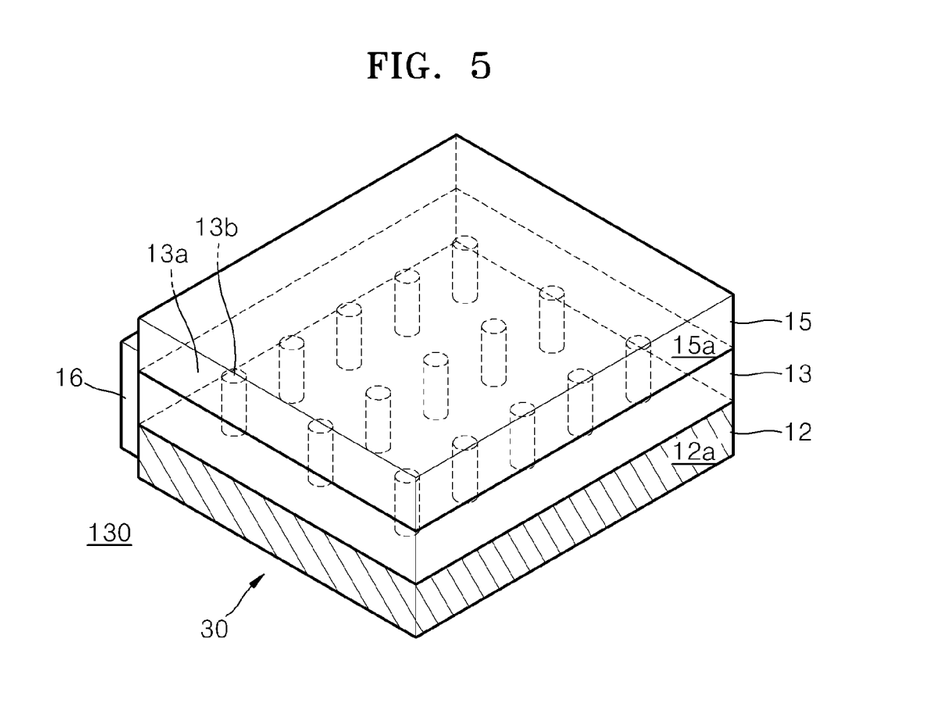
FIG. 5 is a perspective view of a structure of an acousto-optic device according to an example of the invention.

FIG. 5 is a perspective view of a structure of an acousto-optic device 130 including an acousto-optic medium 30 according to example of the invention. Referring to FIG. 5, the acousto-optic medium 30 includes the first layer 12 formed of the first material 12a, the third layer 15 formed of the fourth material 15a, and the second layer 13 including the second material 13a generally filled between the first layer 12 and the third layer 15, and the third material 13b regularly arranged in the second material 13a. For example, as shown in FIG. 5, the third material 13b may be formed to pass through the second material 13a and contact the first layer 12 and the third layer 15. However, the third material 13b may have a sphere or cylinder shape in which the third material 13b is regularly distributed in the second material 13a. The third material 13b may be regularly arranged in a matrix or hive shape in the second material 13a. In this case, light propagating in the acousto-optic medium 30 repeatedly passes through the second material 13a and the third material 13b, and thus the second material 13a and the third material 13b are alternately disposed.

Like in FIGS. 1 and 2, each of the first through fourth materials 12a, 13a, 13b, and 15a of FIG. 5 may include a material selected from the group consisting of a gain material, an acousto-optic material, a dielectric, and a metal. If the third material 13b is regularly arranged in the second material 13a, like FIG. 4, one of the second material 13a and the third material 13b may include a metal. The remainder of construction and the operation of the acousto-optic device 130 of FIG. 5 may be the same as that of the acousto-optic devices 100, 110, and 120 of FIGS. 1-4. Although the sonic wave generator 16 of FIG. 5 is disposed directly on one side surface of the acousto-optic medium 30, the sonic wave generator 16 may be disposed on a top surface of a substrate as shown in FIG. 2.

In the acousto-optic devices 100, 110, 120, and 130 described above, light may propagate in the second layer 13 after being incident onto the third layer 15 of the acousto-optic mediums 10, 20, and 30. In this case, the acousto-optic devices 100, 110, 120, and 130 may further include an optical coupling device that guides light emitted from an external light source to the second layer 13 through the third layer 15 as described below.

Figure 6A:
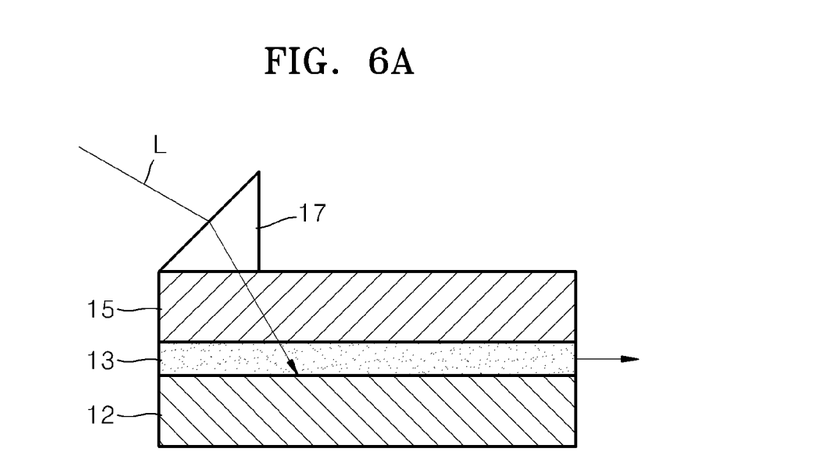
FIGS. 6A and 6B illustrate optical coupling devices used to make light incident onto an acousto-optic medium.
Figure 6B:
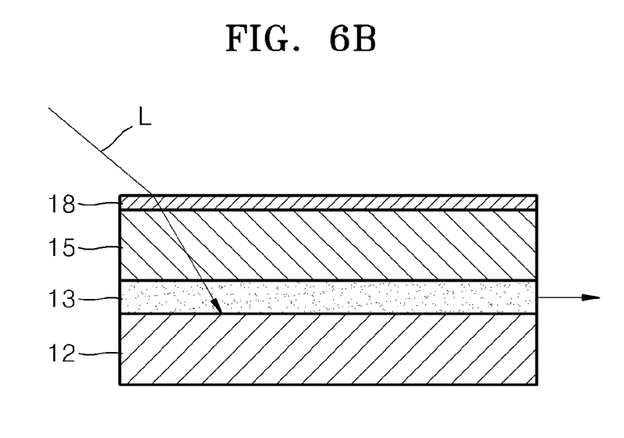

FIGS. 6A and 6B illustrate optical coupling devices used to make light incident onto the acousto-optic mediums 10, 20, and 30 in FIGS. 1-5. Referring to FIG. 6A, for example, a prism 17 may be used as the optical coupling device. The prism 17 may be disposed on a top surface of the acousto-optic mediums 10, 20, and 30, i.e., on a top surface of the third layer 15.

If the acousto-optic mediums 10, 20, and 30 include the first layer 12 and the second layer 13 only, the prism 17 may be disposed on a top surface of the second layer 13. The prism 17 may refract light emitted from an external light source and guide the refracted light to the second layer 13 of the acousto-optic mediums 10, 20, and 30.

As shown in FIG. 6B, a diffraction grating layer 18, instead of the prism 17, may be used as the optical coupling device. The diffraction grating layer 18 having a fine diffraction pattern with a uniform period may diffract incident light and guide the diffracted light to the second layer 13 of the acousto-optic mediums 10, 20, and 30. Although the diffraction grating layer 18 is disposed on an entire top surface of the third layer 15 in FIG. 6B, the diffraction grating layer 18 may be disposed on only a part of the top surface of the third layer 15. If the acousto-optic mediums 10, 20, and 30 include the first layer 12 and the second layer 13 only, the diffraction grating layer 18 may be disposed on the top surface of the second layer 13. In addition to the prism 17 or the diffraction grating layer 18, an optical device, such as a Fresnel lens, a microlens array, a refractive lens (for example, a convex lens), a slit, etc., may be used as the optical coupling device.

The acousto-optic mediums 10, 20, and 30 may be applied in various fields. For example, the acousto-optic devices 100, 110, 120, and 130 may adjust an intensity of 0th order diffracted light according to a diffraction level of light, so that the acousto-optic mediums 10, 20, and 30 may operate as an optical modulator of the 0th order diffracted light. For example, if sonic waves are not applied to the acousto-optic mediums 10, 20, and 30, incident light is not diffracted, so that the incident light passes through the acousto-optic mediums 10, 20, and 30 without a significant loss. However, if incident light is diffracted by applying sonic waves to the acousto-optic mediums 10, 20, and 30, 1st order diffracted light is generated so that an intensity of 0th order diffracted light passing through the acousto-optic mediums 10, 20, and 30 will decrease. If more energy is distributed to the 1st order diffracted light according to a diffraction level, the intensity of the 0th order diffracted light will further decrease. Thus, the acousto-optic devices 100, 110, 120, and 130 may function as an optical modulator that amplitude-modulates the intensity of the 0th order diffracted light.

Furthermore, the acousto-optic devices 100, 110, 120, and 130 may be applied to an optical scanner that deflects incident light to a predetermined angle by varying a diffraction angle of 1st order diffracted light. In particular, when the acousto-optic devices 100, 110, 120, and 130 having a high diffraction angle are applied to the optical scanner, an operational range (i.e., a scanning range) of the optical scanner may be increased so that a structure of an optical system used in the optical scanner becomes simple. In particular, a separate optical system that would otherwise be required to increase the operational range is not needed.

Figure 7:
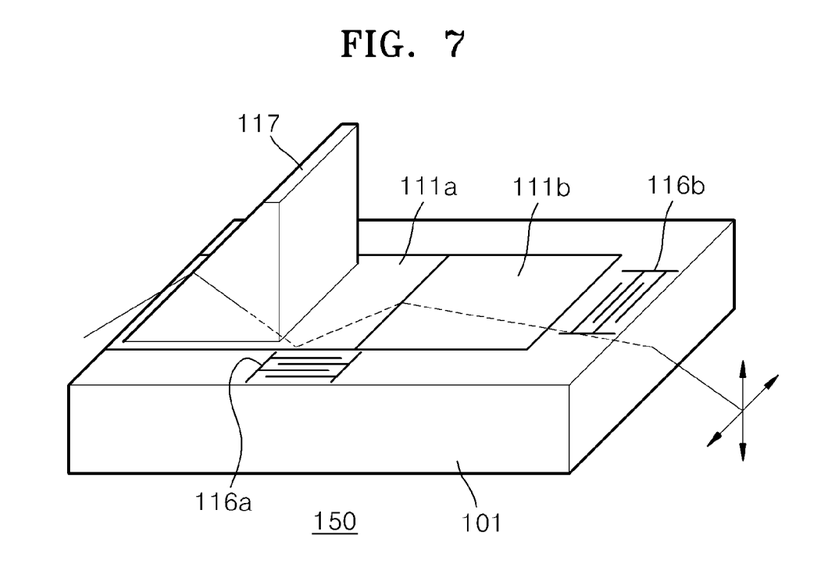
FIG. 7 is a perspective view of an optical scanner including an acousto-optic device according to an example of the invention.

FIG. 7 is a perspective view of an optical scanner 150 including the acousto-optic devices 100, 110, 120, and 130 according to an example of the invention. Referring to FIG. 7, the optical scanner 150 includes a substrate 101, a first acousto-optic medium 111a disposed in the substrate 101, a second acousto-optic medium 111b disposed in the substrate 101 and adjacent to the first acousto-optic medium 111a, an optical coupling device 117 making light incident on the first acousto-optic medium 111a, a first sonic wave generator 116a that applies sonic waves to the first acousto-optic medium 111a, and a second sonic wave generator 116b that applies sonic waves to the second acousto-optic medium 111b. The first sonic wave generator 116a and the second sonic wave generator 116b are disposed on the substrate 101 adjacent to side surfaces of the first acousto-optic medium 111a and the second acousto-optic medium 111b, respectively. The first acousto-optic medium 111a and the second acousto-optic medium 111b may be any one of the acousto-optic mediums 10, 20, and 30. Although a prism is shown as the optical coupling device 117 in FIG. 7, other than the prism, other optical devices, such as a diffraction grating layer, a Fresnel lens, a microlens array, a refractive lens (for example, a convex lens), a slit, etc., may be used as the optical coupling device 117.

The first acousto-optic medium 111a and the first sonic wave generator 116a are configured as a first acousto-optic device that may be configured to deflect light in a horizontal direction. The second acousto-optic medium 111b and the second sonic wave generator 116b are configured as a second acousto-optic device that may be configured to deflect light in a vertical direction. That is, as shown in FIG. 7, light incident onto the first acousto-optic medium 111a through the optical coupling device 117 is deflected in a horizontal direction in the first acousto-optic medium 111a by the first acousto-optic device, deflected in a vertical direction in the second acousto-optic medium 111b by the second acousto-optic device, and then output. Therefore, the optical scanner 150 modulates an intensity and a frequency of an alternating current (AC) applied to the first sonic wave generator 116a and the second sonic wave generator 116b, the incident light may be horizontally and/or vertically scanned within a predetermined angle range.

Although the optical scanner 150 of FIG. 7 includes both the first acousto-optic device and the second acousto-optic device, in another example, the optical scanner 150 may include only one acousto-optic device that scans light in only the horizontal direction or only the vertical direction, or may include a plurality of acousto-optic devices that each scan light in only the horizontal direction and/or a plurality of acousto-optic devices that each scan light in only the vertical direction. Providing such a plurality of acousto-optic devices that each scan light in only one direction makes it possible to increase the scanning range in that direction. The optical scanner 150 of FIG. 7 may be applied to a laser image projecting apparatus, a laser printer, or any other apparatus known in the art that scans light.

The acousto-optic devices 100, 110, 120, and 130 may also be applied to a two-dimensional/three-dimensional (2D/3D) conversion stereoscopic image display apparatus as described below.

Figure 8:
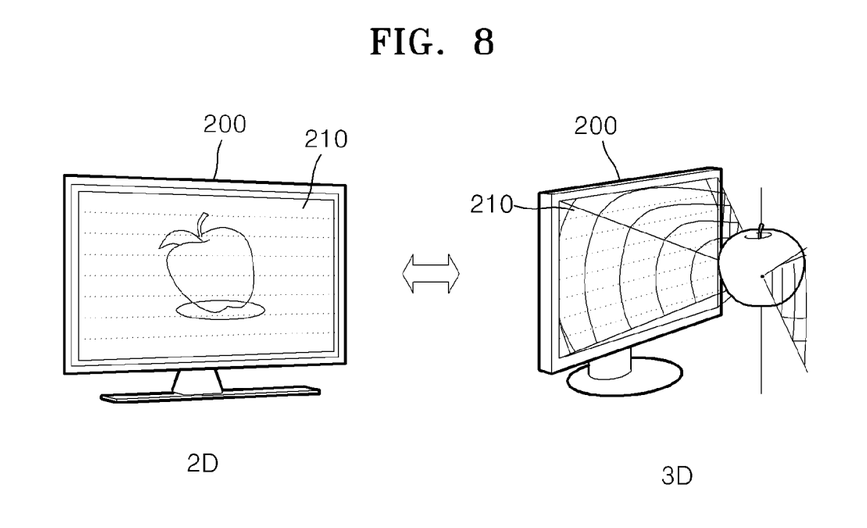
FIG. 8 illustrates an acousto-optic device applied to a two-dimensional/three-dimensional (2D/3D) conversion stereoscopic image display apparatus according to an example of the invention.

FIG. 8 illustrates the acousto-optic devices 100, 110, 120, and 130 applied to a 2D/3D conversion stereoscopic image display apparatus according to an example of the invention. Referring to FIG. 8, a plurality of acousto-optic devices 210 that have the same height as a pixel of a display panel 200 and a same width as a display surface of the display panel 200 are manufactured, and the acousto-optic devices 210 are arrayed on a surface of the display panel 200 to form an array in a vertical direction. In this regard, the acousto-optic devices 210 may be any of the acousto-optic devices 100, 110, 120, and 130. Thus, each acousto-optic device 210 may correspond to one pixel row of the display panel 200, and may deflect an image displayed on one pixel row of the display panel 200 in a predetermined direction. Alternatively, one acousto-optic device 210 may correspond to a plurality of pixels forming a part of one pixel row of the display panel 200.

For example, if sonic waves are not applied to the acousto-optic mediums of the acousto-optic devices 210, an image displayed on each pixel row of the display panel 200 is not deflected and passes through the array of the acousto-optic devices 210. In this case, as illustrated on the left side of FIG. 8, the 2D/3D conversion stereoscopic image display apparatus operates in a 2D display mode. Alternatively, in a multi-view and stereoscopic image 3D display mode, sonic waves are applied to the array of the acousto-optic devices 210, causing each of the acousto-optic devices 210 to deflect the image displayed on one pixel row to generate a plurality of information beams having a plurality of directions. For example, some of the acousto-optic devices 210 may deflect images to a viewer's right eye, and other ones of the acoustooptic devices 210 may deflect images to a viewer's left eye. Thus, as illustrated on the right side of FIG. 8, a viewer may watch a 3D image.

The acousto-optic devices 100, 110, 120, and 130 may also be applied to a holographic 3D display apparatus as described below.

Figure 9:
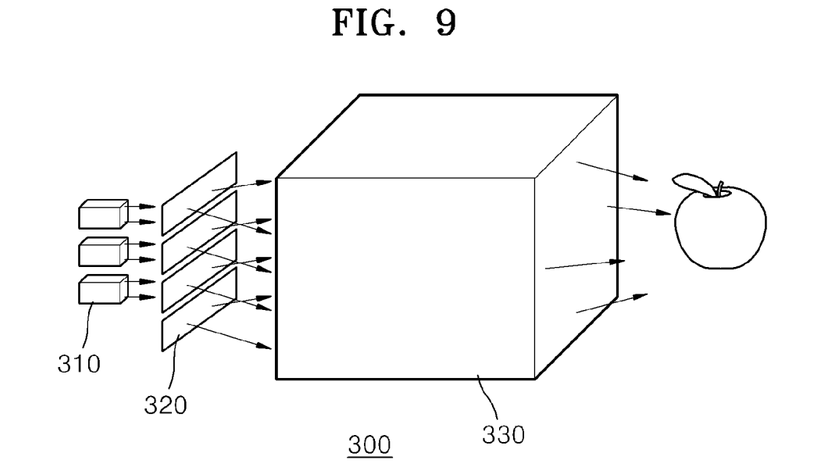
FIG. 9 illustrates an acousto-optic device applied to a holographic 3D display apparatus according to an example of the invention.

FIG. 9 illustrates the acousto-optic devices 100, 110, 120, and 130 applied to a holographic 3D display apparatus 300 according to an example of the invention. For example, as illustrated in FIG. 9, the holographic 3D display apparatus 300 includes a light source 310, an array of a plurality of acousto-optic devices 320, and a projection optical system 330. The light source 310 may be an array of a plurality of lasers. Each of the acousto-optic devices 320 is manufactured to extend in a horizontal direction, and the acousto-optic devices 320 are arrayed in a vertical direction. Each acousto-optic device 320 may correspond to one hologram row in a horizontal direction of a hologram image to be displayed by the holographic 3D display apparatus 300. Alternatively, one acousto-optic device 320 may correspond to a part of one hologram row in the horizontal direction of the hologram image to be displayed by the holographic 3D display apparatus 300. Hologram rows that are diffracted from the acousto-optic devices 320 may be projected in a predetermined space by the projection optical system 330 and may form a stereoscopic image.

The acousto-optic devices 100, 110, 120, and 130 may also be applied to a sensor that detects an amount of a specific chemical material or bio material, or whether the specific chemical material or bio material exists or not as described below.

Figure 10A:
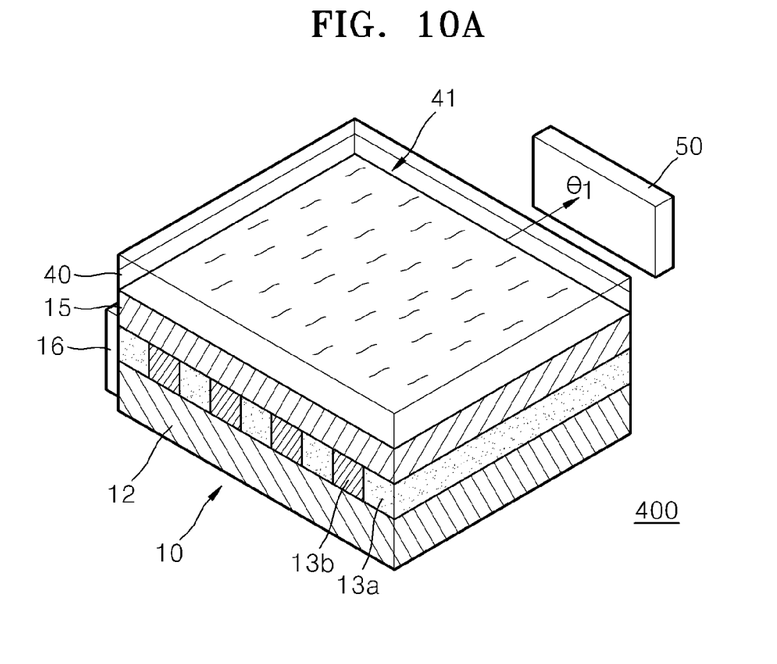
FIGS. 10A and 10B are perspective views of a sensor including an acousto-optic device according to an example of the invention.

FIG. 10A are perspective views of a sensor 400 including the acousto-optic devices 100, 110, 120, and 130 according to an example of the invention. Referring to FIG. 10A, the sensor 400 includes the acousto-optic medium 10 of FIG. 1, the sonic wave generator 16 of FIG. 1, a container 40 disposed on a top surface of the acousto-optic medium 10 and containing a sample 41, and an optical detector 50 that detects light diffracted by the acousto-optic medium 10. Although the acousto-optic device 100 includes the acousto-optic medium 10 and the sonic wave generator 16 shown in FIG. 1, the acousto-optic devices 110, 120, and 130 may be used according to other examples. Although not shown, a probe for capturing a specific target material in the sample 41 may be further disposed on a bottom surface of the container 40 (i.e., a top surface of the acousto-optic medium 10).

If a target material is not included in the sample 41, light incident onto the acousto-optic medium 10 is diffracted a diffraction angle θ1 and detected by the optical detector 50 as shown in FIG. 10A while sonic waves are applied to the acousto-optic medium 10. In this regard, a diffraction angle θ varies depending on a dielectric constant combination of the third layer 15 and the sample 41 and a wavelength of the sonic waves.

Figure 10B:
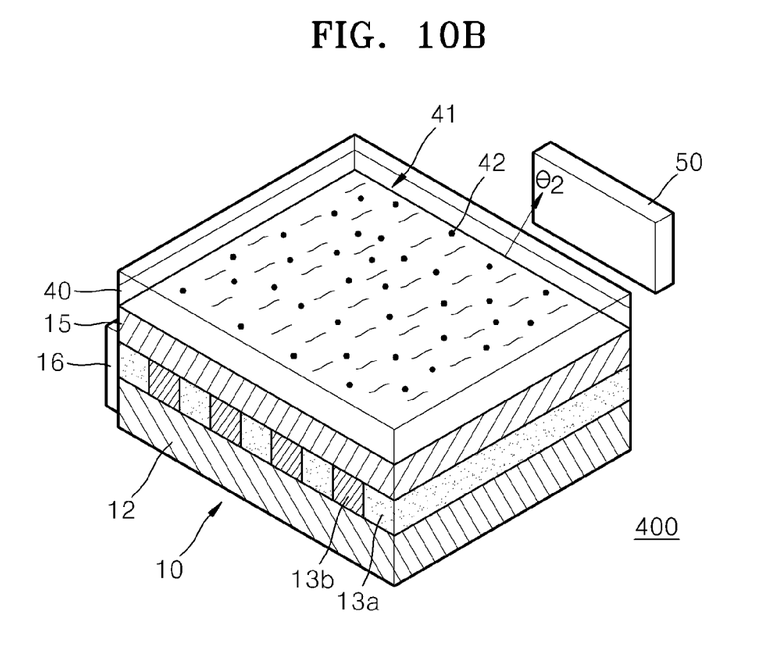

If a target material 42 included in the sample 41 is captured by the probe as shown in FIG. 10B, since the dielectric constant combination of the third layer 15 and the sample 41 and the wavelength of the sonic waves vary due to presence of the target material 42, a diffraction angle of the light incident onto the acousto-optic medium 10 may change to a diffraction angle θ2 and/or a diffraction intensity thereof may decrease. Therefore, it is possible to determine whether the target material 42 is included in the sample 41 and calculate an amount of the target material 42 according to the change in the diffraction angle and/or the diffraction intensity.

While this disclosure has been particularly shown and described with reference to examples thereof, it will be understood by those skilled in the art that various changes in form and details may be made in these examples without departing from the spirit and scope of the invention as defined by the claims and their equivalents. It should be understood that the examples described herein should be considered in a descriptive sense only, and not for purposes of limitation. Descriptions of features or aspects in each example are to be considered as being applicable to similar features or aspects in other examples. Suitable results may be achieved if the described techniques are performed in a different order and/or if components in a described system, architecture, device, or circuit are combined in a different manner and/or replaced or supplemented by other components or their equivalents. Therefore, the scope of the invention is defined not by the detailed description of the disclosure, but by the claims and their equivalents, and all variations within the scope of the claims and their equivalents are to be construed as being included in the invention.

What is claimed is:

1. An acousto-optic device comprising:
an acousto-optic medium having a multi-layer nanostructure; and
a sonic wave generator configured to apply sonic waves to the acousto-optic medium having the multi-layer nanostructure,
wherein the acousto-optic medium having the multi-layer nanostructure comprises
a second layer formed of a second material and a third material that have different dielectric constants, and
a first layer disposed on a first surface of the second layer and formed of a first material, and/or a third layer disposed on a second surface of the second layer and formed of a fourth material, and
wherein the second layer comprises a plurality of pieces of the second material and a plurality of pieces of the third material that repeatedly alternate with each other in a direction parallel to the first surface of the second layer and the second surface of the second layer.

2. The acousto-optic device of claim 1, wherein the first material, the second material, the third material, and the fourth materials comprise a combination of at least two materials selected from the group consisting of:
again material having again characteristic enabling optical amplification of light;
an acousto-optic material exhibiting an acousto-optic effect;
a dielectric that is not a gain material and is not an acousto-optic material; and
a material having a dielectric constant with a real part having a negative value.

3. The acousto-optic device of claim 2, wherein the gain material having a gain characteristic enabling the optical amplification of light comprises at least one material selected from the group consisting of a group III-V semiconductor selected from the group consisting of GaN, Al1 xGaxN, and In1 xGaxN (0<x<1), a quantum well structure or a quantum dot structure comprising the group III-V semiconductor, zinc oxide, CdS, an organic crystal, and a gain dye.

4. The acousto-optic device of claim 2, wherein the dielectric that is not a gain material and is not an acousto-optic material comprises at least one material selected from the group consisting of SiO2 and air.

5. The acousto-optic device of claim 2, wherein the material having a dielectric constant with a real part having a negative value comprises one material selected from the group consisting of a metal selected from the group consisting of Al, Ag, Au, Cu, Na, Ka, and an alloy of any one or more of Al, Ag, Au, Cu, Na, and Ka, an oxide selected from the group consisting of indium tin oxide (ITO), aluminum-doped zinc oxide (AZO), gallium zinc oxide (GZO), and indium zinc oxide (IZO), a nitride selected from the group consisting of titanium nitride (TiN), zirconium nitride (ZrN), tantalum nitride (TaN), and hafnium nitride (HfN), and graphene.

6. The acousto-optic device of claim 2, wherein at least one of the first material, the second material, the third material, and the fourth material has a dielectric constant with a real part having a negative value.

7. The acousto-optic device of claim 1, wherein a period at which the plurality of pieces of the second material and the plurality of pieces of the third material repeatedly alternate with each other is smaller than a wavelength of visible light in air.

8. The acousto-optic device of claim 1, wherein each of an aspect ratio of each of the plurality of pieces of the second material and an aspect ratio of each of the plurality of pieces of the third material is not greater than 4.

9. The acousto-optic device of claim 1, wherein each of the plurality of pieces of the second material and the plurality of pieces of the third material has a bar shape.

10. The acousto-optic device of claim 1, wherein the sonic wave generator is disposed on a side surface of the acousto-optic medium having the multi-layer nanostructure that is perpendicular to the first surface of the second layer and the second surface of the second layer.

11. The acousto-optic device of claim 1, further comprising:
a substrate contacting at least a side surface of the acousto-optic medium having the multi-layer nanostructure that is perpendicular to the first surface of the second layer and the second surface of the second layer,
wherein the sonic wave generator is disposed on a surface of the substrate that is parallel to the first surface of the second layer and the second surface of the second layer adjacent to the side surface of the acousto-optic medium having the multi-layer nanostructure.

12. The acousto-optic device of claim 1, wherein the plurality of pieces of the second material and the plurality of pieces of the third material repeatedly alternate with each other in a direction perpendicular to the first surface of the second layer and the second surface of the second layer.

13. The acousto-optic device of claim 12, wherein:
each of the first material, the second material, the third material, and the fourth material comprises a material selected from the group consisting of a gain material having a gain characteristic enabling optical amplification of light, an acousto-optic material exhibiting an acousto-optic effect, a dielectric that is not a gain material and is not an acousto-optic material, and a material having a dielectric constant with a real part having a negative value; and
the second material or the third material has a dielectric constant with a real part having a negative value.

14. The acousto-optic device of claim 1, wherein the third material is regularly arranged in the second material.

15. The acousto-optic device of claim 1, further comprising:
an optical coupling device configured to guide light incident onto the acousto-optic medium having the multi-layer nanostructure to enable the light to propagate in the second layer.

16. The acousto-optic device of claim 15, wherein the optical coupling device comprises a prism or a diffraction grating layer disposed on a surface of the acousto-optic medium having the multi-layer nanostructure.

17. A two-dimensional/three-dimensional (2D/3D) conversion stereoscopic image display apparatus comprising:
a display panel; and
an acousto-optic device array disposed on a surface of the display panel to deflect an image to be displayed on the display panel,
wherein the acousto-optic device array comprises a plurality of the acousto-optic device of claim 1.

18. The 2D/3D conversion stereoscopic image display apparatus of claim 17, wherein:
each of the plurality of acousto-optic devices of the acousto-optic device array extends in a horizontal direction; and
the plurality of acousto-optic devices are arrayed in a vertical direction.

19. The 2D/3D conversion stereoscopic image display apparatus of claim 18, wherein each of the plurality of acousto-optic devices of the acousto-optic device array corresponds to one pixel row of the display panel.

20. A holographic display apparatus comprising:
a light source configured to emit light;
an acousto-optic device array configured to deflect the light emitted from the light source, and comprising a plurality of the acousto-optic device of claim 1; and
a projection optical system configured to project the light deflected by the acousto-optic device array.

21. The holographic display apparatus of claim 20, wherein:
each of the plurality of acousto-optic devices of the acousto-optic device array extends in a horizontal direction; and
the plurality of acousto-optic devices are arrayed in a vertical direction.

22. The holographic display apparatus of claim 21, wherein:
the plurality of acousto-optic devices generate hologram rows in a horizontal direction of a hologram image displayed by the holographic display apparatus; and
each of the plurality of acousto-optic devices corresponds to one of the hologram rows.

23. A sensor comprising:
the acousto-optic device of claim 1;
a container disposed on a surface of the acousto-optic medium having the multi-layer nanostructure and configured to contain a sample; and
an optical detector configured to detect light diffracted in a combination of the acousto-optic medium having the multi-layer nanostructure and the sample in the container.

24. An optical scanner comprising:
a substrate;
a first acousto-optic device;
a second acousto-optic device; and
an optical coupling device configured to make light incident on the first acousto-optic device,
wherein the first acousto-optic device comprises
a first acousto-optic medium disposed in the substrate, and
a first sonic wave generator disposed on a surface of the substrate adjacent to a side surface of the first acousto-optic medium that is perpendicular to the surface of the substrate,
wherein the second acousto-optic device comprises
a second acousto-optic medium disposed in the substrate and adjacent to the first acousto-optic medium, and a second sonic wave generator disposed on the surface of the substrate adjacent to a side surface of the second acousto-optic that is perpendicular to the surface of the substrate, wherein each of the first acousto-optic medium and the second acousto-optic medium comprises
- a second layer formed of at least two materials that have different dielectric constants and alternate with each other, and
- a first layer disposed on a first surface of the second layer and formed of a first material, and/or a third layer disposed on a second surface of the second layer and formed of a fourth material, and wherein the first surface of the second layer and the second surface of the second layer are parallel to the surface of the substrate.

25. The optical scanner of claim 24, wherein:
the second layer comprises a plurality of pieces of a second material and a plurality of pieces of a third material that repeatedly alternate with each other; and
the first material, the second material, the third material, and the fourth material comprise a combination of at least two materials selected from the group consisting of
- a gain material having a gain characteristic enabling optical amplification of light,
- an acousto-optic material exhibiting an acousto-optic effect,
- a dielectric material that is not a gain material and is not an acousto-optic material, and
- a material having a dielectric constant with a real part having a negative value.

26. The optical scanner of claim 25, wherein:
the plurality of pieces of the second material and the plurality of pieces of the third material repeatedly alternate with each other in a direction parallel to the first surface of the second layer and the second surface of the second layer;
the second material and the third have different dielectric constants; and
at least one of the first material, the second material, the third material, and the fourth material has a dielectric constant with a real part having a negative value.

27. The optical scanner of claim 25, wherein:
the plurality of pieces of the second material and the plurality of pieces of the third material repeatedly alternate with each other in a direction perpendicular to the first surface of the second layer and the second surface of the second layer;
the second material and the third material have different dielectric constants; and
at least one of the first material, the second material, the third material, and the fourth material has a dielectric constant with a real part having a negative value.

28. The optical scanner of claim 24, wherein:
the first acousto-optic device is configured to deflect incident light in a first direction; and
the second acousto-optic device is configured to deflect the incident light deflected by the first acousto-optic device in a second direction perpendicular to the first direction.

29. An acousto-optic device comprising:
an acousto-optic medium; and
a sonic wave generator configured to apply sonic waves to the acousto-optic medium,
wherein the acousto-optic medium comprises
- a first layer comprising a first material and a second material that have different dielectric constants and alternate with each other to form a nanostructure in the first layer, and
- a second layer disposed on a surface of the first layer and comprising a third material, and
wherein the first layer comprises a plurality of pieces of the first material and a plurality of pieces of the second material that repeatedly alternate with each other in a direction parallel to the surface of the first layer.

30. The acousto-optic device of claim 29, wherein the first material and the second material alternate with each other at a period that is smaller than a wavelength of light to be controlled by the acousto-optic device.

31. The acousto-optic device of claim 29, wherein:
at least one of the first material, the second material, and the third material comprises a metal; and
at least one of the first material, the second material, and the third material does not comprise a metal.

32. The acousto-optic device of claim 31, wherein the metal is selected from the group consisting of Al, Ag, Au, Cu, Na, Ka, and an alloy of any one or more of Al, Ag, Au, Cu, Na, and Ka.

33. The acousto-optic device of claim 31, wherein the acousto-optic medium generates surface plasmons in an interface between the first layer and the second layer from light that is incident on the acousto-optic medium.

34. The acousto-optic device of claim 29, wherein the first material, the second material, and the third material comprise a combination of at least two materials selected from the group consisting of:
a gain material having a gain characteristic enabling optical amplification of light;
an acousto-optic material exhibiting an acousto-optic effect;
a dielectric that is not a gain material and is not an acousto-optic material; and
a material having a dielectric constant with a real part having a negative value.

35. The acousto-optic device of claim 1, further comprising:
a substrate comprising a surface on which the first layer is disposed.

* * * * *